(12) United States Patent
Van Der Puy

(10) Patent No.: US 8,071,826 B2
(45) Date of Patent: Dec. 6, 2011

(54) PROCESS FOR THE PREPARATION OF 2,3,3,3-TETRAFLUOROPROPENE (HFO-1234YF)

(75) Inventor: Michael Van Der Puy, Amherst, NY (US)

(73) Assignee: Honeywell International Inc., Morristown, NJ (US)

( * ) Notice: Subject to any disclaimer, the term of this patent is extended or adjusted under 35 U.S.C. 154(b) by 332 days.

(21) Appl. No.: 12/391,477

(22) Filed: Feb. 24, 2009

(65) Prior Publication Data

US 2009/0253946 A1 Oct. 8, 2009

Related U.S. Application Data

(60) Provisional application No. 61/042,376, filed on Apr. 4, 2008.

(51) Int. Cl.
*C07C 21/18* (2006.01)

(52) U.S. Cl. ........ 570/186; 570/159; 570/166; 570/169; 570/172

(58) Field of Classification Search .................. None
See application file for complete search history.

(56) References Cited

U.S. PATENT DOCUMENTS

| | | | | |
|---|---|---|---|---|
| 2,931,840 | A * | 4/1960 | Marquis | 570/159 |
| 2,996,555 | A | 8/1961 | Rausch | 570/156 |
| 3,446,859 | A | 5/1969 | Weil et al. | 570/159 |
| 3,819,731 | A | 6/1974 | Pitt et al. | 570/187 |
| 4,900,874 | A | 2/1990 | Ihara et al. | 570/142 |
| 6,080,900 | A * | 6/2000 | Shibanuma et al. | 570/168 |
| 7,345,209 | B2 | 3/2008 | Mukhopadhyay et al. | 570/157 |
| 7,420,094 | B2 | 9/2008 | Petrov et al. | 570/151 |
| 7,592,494 | B2 * | 9/2009 | Tung et al. | 570/164 |
| 2006/0258891 | A1 * | 11/2006 | Mukhopadhyay et al. | 570/172 |
| 2009/0030244 | A1 | 1/2009 | Merkel et al. | 570/135 |
| 2009/0030245 | A1 | 1/2009 | Ma et al. | 570/136 |

FOREIGN PATENT DOCUMENTS

| | | |
|---|---|---|
| WO | WO 2008/030440 | 3/2008 |
| WO | WO 2008/054778 | 5/2008 |
| WO | WO 2008/054779 | 5/2008 |
| WO | WO 2008/054781 | 5/2008 |
| WO | WO 2008/054782 | 5/2008 |
| WO | WO 2008/060614 | 5/2008 |
| WO | WO 2009/003084 | 12/2008 |
| WO | WO 2009/003085 | 12/2008 |
| WO | WO 2009/003157 | 12/2008 |

OTHER PUBLICATIONS

U.S. Appl. No. 60/953,528, filed Aug. 2, 2007.
U.S. Appl. No. 61/038,327, filed Mar. 20, 2008.
U.S. Appl. No. 61/053,518, filed May 15, 2008.
U.S. Appl. No. 61/073,186, filed Jun. 17, 2008.
U.S. Appl. No. 61/085,141, filed Jul. 31, 2008.
U.S. Appl. No. 61/091,034, filed Aug. 22, 2008.
U.S. Appl. No. 61/113,477, filed Nov. 11, 2008.
U.S. Appl. No. 12/338,466, filed Dec. 18, 2008.
Knunyants, I.L., et al. "Reactions of Fluoro Olefins, Communication 13. Catalytic Hydrogenation of Perfluoro Olefins." Izvestiya Akademii Nauk SSSR, Otdelenie Khimicheskikh Nauk, No. 8, pp. 1412-1418, Aug. 1960.
Yang, Zhen-Yu. "Preparation of Highly Fluorinated Cyclopropanes and Ring-Opening Reactions With Halogens." Journal of Organic Chemistry. 2003. 68. pp. 4410-4416.
Grzybowska, Barbara A., et al. "The Reaction of Methylene with Tetrafluoroethylene." J. Chem. Soc., 1963, pp. 746-748.
Sheremet'ev, S. K., et al. "High-Energy Processes in Polyfluoroalkane Transformations. VII. Thermal Transformation of ChloroMethane and ChloroDifluoromethane." Zh. Obshch. Khim. 1989, 59(3), pp. 631-636.
Casas, F., et al. "Fluorinated Cyclopropanes. III. The Reactions of Methylene With Mono- 1,1-di-, and Trifluoroethylene." J. Chem. Coc. 1965, pp. 1141-1148.

* cited by examiner

*Primary Examiner* — Sudhakar Katakam
(74) *Attorney, Agent, or Firm* — Bruce Bradford

(57) ABSTRACT

A process for the preparation of 2,3,3,3-tetrafluoropropene (HFO-1234yf). HFO-1234yf is a refrigerant with low global warming potential. A process comprises a) reacting chlorotrifluoroethylene with a methyl halide to form an intermediate product stream; and b) reacting the intermediate product stream with hydrogen fluoride to thereby produce a result comprising 2,3,3,3-tetrafluoropropene.

21 Claims, No Drawings

PROCESS FOR THE PREPARATION OF 2,3,3,3-TETRAFLUOROPROPENE (HFO-1234YF)

CROSS REFERENCE TO RELATED APPLICATION

This application claims the benefit of U.S. Provisional patent application Ser. No. 61/042,376, file Apr. 4, 2008, which is incorporated herein by reference.

BACKGROUND OF THE INVENTION

1. Field of the Invention

The present invention relates to processes for the preparation of a tetrafluorinated propene. More specifically, this invention concerns processes for the preparation of the hydrofluoroolefin 2,3,3,3-tetrafluoropropene (HFO-1234yf). HFO-1234yf is a refrigerant with low global warming potential.

2. Description of the Related Art

Fluorocarbon based fluids have found widespread use in industry in a number of applications, including as refrigerants, aerosol propellants, blowing agents, heat transfer media, and gaseous dielectrics. Because of the suspected environmental problems associated with the use of some of these fluids, including the relatively high global warming potentials associated therewith, it is desirable to use fluids having the lowest possible greenhouse warming potential in addition to zero ozone depletion potential. Thus there is considerable interest in developing environmentally friendlier materials for the applications mentioned above. Tetrafluoropropenes, having zero ozone depletion and low global warming potential, have been identified as potentially filling this need. However, the toxicity, boiling point, and other physical properties in this class of chemicals vary greatly from isomer to isomer. One tetrafluoropropene having valuable properties is 2,3,3,3-tetrafluoropropene (HFO-1234yf). Thus, there is a need for new manufacturing processes for the production of tetrafluoropropenes and in particular 2,3,3,3-tetrafluoropropene.

U.S. Pat. Nos. 3,819,731 and 3,446,859 disclose the reaction of methyl chloride with either trichloroethylene or tetrachloroethylene in a hot tube reactor to form $CCl_2=CHCH_2Cl$ or $CCl_2=CClCH_2Cl$, respectively. The reaction is believed to occur via a radical process. Tetrafluoroethylene was reacted with methylene produced by photolysis of ketene, resulting in tetrafluorocyclopropane which isomerizes in part to give a tetrafluoropropene believed to be $HCF_2CH=CF_2$, and not $CF_3CF=CH_2$ (J. Chem. Soc., 1963, 746). Methyl chloride has been pyrolyzed along with $CF_2HCl$ at 800° C. to give a product stream that contained about 15% of $CF_3CF=CH_2$ (U.S. Pat. No. 2,931,840). HFO-1234yf has also been made by the dehydrofluorination of $CF_3CHFCH_2F$ with KOH in butyl ether (Chem. Abstr. 1961:349f), and by the reaction of $CF_3CF_2CH_2OH$ with hydrogen (U.S. Pat. No. 4,900,874).

In would be advantageous to have a process for the manufacture of HFO-1234yf that is continuous, vapor phase, and which uses readily available raw materials. As the prior art processes fail in one or more of these desirable features, more advantageous routes are desired, especially those amenable to large scale manufacture.

In general, the process of this invention involves feeding together into a reactor at elevated temperature, a mixture of chlorotrifluoroethylene (CTFE) with a methyl halide to form an intermediate product stream. This step produces HFO-1234yf precursors, such as $CF_2=CFCH_2Cl$, that are then fed into a second reactor along with HF, which converts the precursors into HFO-1234yf.

SUMMARY OF THE INVENTION

The invention provides a process for the preparation of 2,3,3,3-tetrafluoropropene which comprises:

a) reacting chlorotrifluoroethylene with a methyl halide to form an intermediate product stream; and b) reacting the intermediate product stream with hydrogen fluoride to thereby produce a result comprising 2,3,3,3-tetrafluoropropene.

DESCRIPTION OF THE INVENTION

The first step in the reaction requires reacting chlorotrifluoroethylene with a methyl halide to form an intermediate product stream. The methyl halide may be methyl chloride, methyl fluoride or methyl bromide, however, methyl chloride is preferred. The reactor for the first step consists of a heated empty tube. The material of construction should be inert to by-product HCl and small amounts of HF that are generally formed. Monel, inconel, and nickel are among the best. The first reaction step may be conducted in a vapor phase at a temperature of from about 500° C. to about 1000° C., preferably from about 600° C. to about 900° C. and more preferably from about 650° C. to about 750° C. Methyl halide and CTFE are fed into the first reactor at an approximately equal molar ratio. However, the ratio of CTFE to methyl halide can range from about 0.7 to about 1.5, and preferably from about 0.9 and to about 1.1.

The contact time between the chlorotrifluoroethylene and the methyl halide in the first step a) ranges from more than 0 seconds to about five seconds. Satisfactory results are obtained with contact times that are in the range of from about 0.5 second to about 3 seconds. These contact times may be achieved by adjusting the usual parameters of pressure, temperature, and feed rate.

Effluent from the first reactor is comprised of a mixture of compounds including by-product HCl, unreacted CTFE, unreacted methyl halide, and the reaction products including $C_3H_2ClF_3$ isomers, such as $CF_2=CFCH_2Cl$, $CF_2=CHCHClF$, $CFCl=CHCHF_2$, $HCF_2CF=CHCl$, and chlorotrifluorocyclopropane, $C_3H_3Cl_2F_3$ isomers such as $HCF_2CFClCH_2Cl$ and $HCFClCF_2CH_2Cl$ and dehydrofluorination products such as isomers of $C_3H_2Cl_2F_2$ derived from them.

The reactions are conducted in a continuous mode. Preferably, but not necessarily, the second reaction step b) may be conducted in a second reactor which is of the same or similar configuration to that of the first reactor. Preferably the second reaction step is also conducted in a vapor phase. Preferably both the first and second reaction steps are conducted in a vapor phase.

Preferably the intermediate product stream is reacted in a second reactor and the bulk of these intermediate products are converted into $CF_3CF=CH_2$ as the main product (HFC-245fa, and minor amounts of other hydrofluorocarbons may also be formed). The intermediate product stream of the first reactor is fed, along with HF, into the second reactor which contains a fluorination catalyst such as well known vapor phase fluorination catalysts. Non-limiting examples of such vapor phase fluorination catalysts include activated carbon, activated carbon impregnated with metal salts, chromium oxide (chromia), and fluorinated chromium oxide. Chromium oxide and fluorinated chromium oxide are preferred.

Stoichiometry requires only one mole of HF per mole of CTFE fed into the first reactor, but up to 5 equivalents may be added to adjust flow rates or maximize conversion and yield. Typically 1-2 moles of HF per mole of CTFE are added.

The temperature range for the second step b) depends on catalyst reactivity and stability. In a preferred embodiment, step b) is conducted at a temperature of from about 225° C. to about 575° C. In a more preferred embodiment step b) is conducted at a temperature of from about 275° C. to about 560° C. In a still more preferred embodiment step b) is conducted at a temperature of from about 280° C. to about 550° C.

Typical resulting effluent from the second reactor is comprised of a mixture of primarily HCl, HF, $CF_3CF=CH_2$, and HFC-245fa and minor amounts of methyl chloride, methyl fluoride, $C_3H_2F_4$ isomers, such as $HCF_2CF=CHF$, and chlorofluoropropenes.

Preferably HFO-1234yf is thereafter separated from the result, such as by distillation. Since the boiling points of the two principle products differ widely, it is not difficult to separate HFO-1234yf and HFC-245fa via distillation of the crude product mixture. It is however, advantageous to maximize the conversion of the starting materials.

EXAMPLE 1

Chlorotrifluoroethylene (CTFE) vapor (0.01 mol/min) and methyl chloride (0.01 mol/min) are mixed and fed into a 50 cc nickel tube reactor (R1), heated electrically to 650° C. at a residence time of about 2 seconds. The conversion of chlorotrifluoroethylene is about 90% while the conversion of methyl chloride is about 95%, as determined by analysis of samples taken at the reactor exit. The effluent gases from the first reactor are then fed into a second reactor (R2), along with HF at 0.01 mol/min. The second reactor contains 75 cc of fluorinated chromium oxide catalyst heated to 325° C. The contact time in the second reactor is thus about 5 seconds. The main 3-carbon species in the effluent of the second reactor is $CF_3CF=CH_2$ (72% of the components with more than 2 carbon atoms as determined by GC area % and MS analysis).

EXAMPLE 2

Example 2 is conducted with the first reactor using methyl fluoride instead of methyl chloride. In this case, $CF_3CF=CH_2$ is formed directly, but the conversion is substantially lower for both chlorotrifluoroethylene and methyl fluoride, and the yield of $CF_3CF=CH_2$ (as a percent of materials with more than two carbon atoms) decreases to 37%.

EXAMPLES 3-6

Examples 3-6 are conducted in a manner similar to that of Example 1, using different ratios of reactants and different reaction temperatures. The output table gives the amounts of components after the second fluorination reactor.

| Input table (amounts for materials are mol/min). | | | | |
|---|---|---|---|---|
| No. | CTFE | MeCl | HF | Temp ° C. (R1) | Temp ° C. (R2) |
| 3a | 0.0098 | 0.0110 | 0.015 | 650 | 315 |
| 4a | 0.0099 | 0.0098 | 0.02 | 685 | 335 |
| 5a | 0.0103 | 0.0104 | 0.02 | 725 | 335 |
| 6a | 0.0106 | 0.0111 | 0.029 | 700 | 325 |

| Output table | | | | |
|---|---|---|---|---|
| | CFTE | MeCl | % selectivity (compounds with >2 carbon atoms) | | |
| No. | % conv. | % conv. | HFO-1234yf | HFC-245fa | other |
| 3b | 93 | 93 | 77 | 13 | 10 |
| 4b | 91 | 95 | 75 | 17 | 8 |
| 5b | 99 | 99 | 87 | 6 | 7 |
| 6b | 98 | 95 | 85 | 9 | 6 |

EXAMPLE 7

Chlorotrifluoroethylene (CTFE) vapor (0.01 mol/min) and a methyl halide (0.01 mol/min) are mixed and fed into a 50 cc nickel tube reactor (R1), heated electrically to 650° C. at a residence time of about 2 seconds. The effluent gases from the first reactor are then fed into a second reactor (R2), along with HF at 0.01 mol/min. The second reactor contains 75 cc of fluorinated chromium oxide catalyst heated to 325° C. The contact time in the second reactor is thus about 5 seconds. The main 3-carbon species in the effluent of the second reactor is $CF_3CF=CH_2$.

EXAMPLE 8

Example 7 is conducted several times wherein the methyl halide is methyl fluoride, methyl chloride, and methyl bromide respectively. Similar results are noted.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A process for the preparation of 2,3,3,3-tetrafluoropropene which comprises:
   a) reacting chlorotrifluoroethylene with a methyl halide to form an intermediate product stream; and
   b) reacting the intermediate product stream with hydrogen fluoride to thereby produce a result comprising 2,3,3,3-tetrafluoropropene, wherein the reacting of the intermediate product stream with hydrogen fluoride is conducted in the presence of a fluorination catalyst comprising at least one of activated carbon, activated carbon impregnated with metal salts, chromium oxide, and fluorinated chromium oxide.

2. The process of claim 1 comprising the subsequent step of separating 2,3,3,3-tetrafluoropropene from the result.

3. The process of claim 1 comprising the subsequent step of separating 2,3,3,3-tetrafluoropropene from the result by distillation.

4. The process of claim 1 wherein the methyl halide comprises methyl chloride.

5. The process of claim 1 wherein step a) is conducted in a first reactor and then step b) is conducted in a second reactor.

6. The process of claim 1 wherein steps a) and b) are conducted in a vapor phase.

7. The process of claim 1 wherein step a) is conducted at a temperature of from about 500° C. to about 1000° C.

8. The process of claim 1 wherein step a) is conducted at a temperature of from about 600° C. to about 900° C.

9. The process of claim 1 wherein step a) is conducted at a temperature of from about 650° C. to about 750° C.

10. The process of claim 1 wherein the mole ratio of chlorotrifluoroethylene methyl halide in step a) ranges from about 0.7 to about 1.5.

11. The process of claim 1 wherein the mole ratio of chlorotrifluoroethylene methyl halide in step a) ranges from about 0.9 to about 1.1.

12. The process of claim 1 wherein the contact time between the chlorotrifluoroethylene and the methyl halide in step a) ranges from more than 0 seconds to about five seconds.

13. The process of claim 1 wherein the contact time between the chlorotrifluoroethylene and the methyl halide in step a) ranges from about 0.5 second to about 3 seconds.

14. The process of claim 1 wherein the reacting of the intermediate product stream with hydrogen fluoride is conducted in the presence of a fluorination catalyst.

15. The process of claim 1 wherein the reacting of the intermediate product stream with hydrogen fluoride is conducted in the presence of a fluorination catalyst comprising chromium oxide.

16. The process of claim 1 wherein the reacting of the intermediate product stream with hydrogen fluoride is conducted with at least one mole of hydrogen fluoride per mole of chlorotrifluoroethylene from step a).

17. The process of claim 1 wherein the reacting of the intermediate product stream with hydrogen fluoride is conducted with from about one mole to about two moles of hydrogen fluoride per mole of chlorotrifluoroethylene from step a).

18. The process of claim 1 wherein the reacting of the intermediate product stream with hydrogen fluoride is conducted with from about one mole to about five moles of hydrogen fluoride per mole of chlorotrifluoroethylene from step a).

19. The process of claim 1 wherein step b) is conducted at a temperature of from about 225° C. to about 575° C.

20. The process of claim 1 wherein step b) is conducted at a temperature of from about 275° C. to about 560° C.

21. The process of claim 1 wherein step b) is conducted at a temperature of from about 280° C. to about 550° C.

* * * * *